(12) United States Patent
Takahashi

(10) Patent No.: US 7,455,637 B2
(45) Date of Patent: Nov. 25, 2008

(54) ELECTRONIC ENDOSCOPE WITH HEATER

(75) Inventor: Kazuaki Takahashi, Saitama (JP)

(73) Assignee: Fujinon Corporation, Saitama (JP)

(*) Notice: Subject to any disclaimer, the term of this patent is extended or adjusted under 35 U.S.C. 154(b) by 240 days.

(21) Appl. No.: 11/527,392

(22) Filed: Sep. 27, 2006

(65) Prior Publication Data

US 2007/0073108 A1    Mar. 29, 2007

(30) Foreign Application Priority Data

Sep. 28, 2005  (JP) .................... P2005-282046

(51) Int. Cl.
*A61B 1/05* (2006.01)
(52) U.S. Cl. ...................... 600/169; 359/512
(58) Field of Classification Search ................ 600/169, 600/170, 171, 176; 359/507, 512; 348/340; 433/30, 31

See application file for complete search history.

(56) References Cited

U.S. PATENT DOCUMENTS

| | | | | |
|---|---|---|---|---|
| 3,495,259 A | * | 2/1970 | Rocholl et al. | 219/522 |
| 4,076,018 A | * | 2/1978 | Heckele | 600/168 |
| 5,605,532 A | * | 2/1997 | Schermerhorn | 600/169 |
| 5,647,840 A | * | 7/1997 | D'Amelio et al. | 600/169 |
| 6,866,391 B2 | * | 3/2005 | Krausse | 359/512 |
| 2003/0089702 A1 | * | 5/2003 | Carver et al. | 219/543 |
| 2005/0090749 A1 | * | 4/2005 | Rubbert | 600/473 |

FOREIGN PATENT DOCUMENTS

| | | |
|---|---|---|
| JP | 2003-282847 A | 10/2003 |
| JP | 2003-284686 A | 10/2003 |
| JP | 2006-000282 A | 1/2006 |
| WO | WO-97/31293 A1 | 8/1997 |

* cited by examiner

*Primary Examiner*—John P Leubecker
(74) *Attorney, Agent, or Firm*—Birch, Stewart, Kolasch & Birch, LLP

(57) ABSTRACT

An electronic endoscope comprising a pick-up unit at a distal end of the electronic endoscope, the pick-up unit comprising: an object optical system that brings in image light of a portion to be observed in a body cavity; a solid-state image pick-up device that picks up the image light and outputs image pick-up signals; a cover glass disposed above an image pick-up surface of the solid-state image pick-up device with spacing secured between the cover glass and the image pick-up surface; and a prism, whose incidence plane and emission plane are connected to the object optical system and the cover glass respectively, that guides image light from the object optical system to the pick-up surface, wherein the electronic endoscope further comprises: a heater that is attached to the prism and heats a surface of the cover glass, to which the emission plane is connected, via the prism; and a controller that controls operations of the heater.

4 Claims, 4 Drawing Sheets

ELECTRONIC ENDOSCOPE WITH HEATER

BACKGROUND OF THE INVENTION

1. Field of the Invention

The present invention relates to an electronic endoscope having an image pick-up unit for picking up images in a body cavity incorporated in the distal end thereof.

2. Description of the Related Art

In the related art, medical diagnosis utilizing an electronic endoscope has widely been carried out in a medical field. The distal end, inserted into a body cavity, of the endoscope scope is internally provided with an image pick-up unit having a solid-state image pick-up device such as a CCD, pick-up signals acquired by the CCD are subjected to signal processing by a processor unit, whereby it becomes possible to observe an image (an endoscopic image) in a body cavity via a monitor display.

A pick-up unit incorporated in the electronic endoscope is structured so that it includes a CCD described above and an object optical system for picking up image light at a portion to be observed in a body cavity, which is made incident through an observation window secured at the distal end of the insertion portion, cover glass is disposed on the image pick-up surface of the CCD with an air gap secured, and a prism is connected to the cover glass and the object optical system.

However, the temperature of the distal end of the insertion portion of an endoscope inserted into a body cavity becomes equivalent to the body temperature (to 37° C.). To the contrary, the temperature inside the insertion portion sometimes becomes 40° C. or more, which is higher than the body temperature, due to driven heat of the electronic components such as a CCD. In addition, since rinse water or air may be jetted onto the distal end of the insertion portion where the observation window is stained, a difference in temperature occurs between the surface of the distal end of the insertion portion and the interior thereof. Accordingly, if moisture is contained in the insertion portion, it has been found that condensation may occur on the object optical system and the cover glass.

In particular, the inside surface of the cover glass is liable to become higher in temperature because it is close to the image pick-up surface of the CCD. On the other hand, since the outer surface of the cover glass to which a prism is connected may be rapidly cooled down by jetting of rinse water, condensation may occur on the inner side of the cover glass due to moisture contained in the air gap.

Also, if the endoscope is connected to a processor unit and its power source is turned on when using an electronic endoscope that was being stored, the temperature of the solid-state image pick-up device rises immediately thereafter. However, the temperature of members such as the object optical system, prism, and cover glass gradually rises while obtaining heat of the solid-state image pick-up device and its peripheral circuits. Therefore, since there is a great difference in temperature between the solid-state image pick-up device and the cover glass immediately after the power source is turned on, condensation is apt to occur.

Where condensation occurs in the object optical system, the image is merely blurred, wherein there is no remarkable influence on observation. However, if condensation occurs on the inside surface of the cover glass as described above, water drops become so significant that they can be viewed on an image, and the image quality deteriorates, wherein it becomes difficult to observe.

In order to prevent condensation as described above, such a solid-state image pick-up unit has been proposed, which is devised so that no moisture is permitted to enter the air gap by enclosing the air gap with a material such as ceramic that does not permeate any moisture (Refer to JP-A-2003-282847). Further, such an image pick-up unit for an endoscope has been proposed (Refer to JP-A-2003-284686), in which a heating body such as peripheral circuits of a solid-state image pick-up device is disposed in the vicinity of the cover glass so as to heat the outer surface (the surface to which the prism is connected) of the cover glass.

However, as in the method described in JP-A-2003-282847, even if such a structure is employed which keeps the air gap airtight, and the cover glass is attached with the air gap kept airtight when manufacturing an image pick-up unit, it is not easy to prevent moisture from intruding. Ultimately, water is permitted to intrude due to chronological changes. Also, since the unit is large-scaled by addition of the structure of keeping the air gap airtight, there is only a slight effect although the production cost is increased.

Further, in the method described in JP-A-2003-284686, since the vicinity of the cover glass is merely heated by a heating body, there is a problem that the utilization efficiency of heat is very poor. Therefore, the temperature is raised not only on the outer surface of the cover glass, but also for the entirety of the image pick-up unit. In addition, there is another problem that it takes much time until the outer surface of the cover glass is heated and the method cannot cope with a radical change in temperature.

SUMMARY OF THE INVENTION

The present invention has been made in view of the above-described problems, and an object thereof is to provide an electronic endoscope having an inexpensive construction, which is capable of efficiently and reliably preventing condensation of a cover glass attached to a solid-state image pick-up device.

In order to achieve the above-described object, the present invention relates to an electronic endoscope comprising a pick-up unit at a distal end of the electronic endoscope, the pick-up unit comprising: an object optical system that brings in image light of a portion to be observed in a body cavity; a solid-state image pick-up device that picks up the image light and outputs image pick-up signals; a cover glass disposed above an image pick-up surface of the solid-state image pick-up device with spacing secured between the cover glass and the image pick-up surface; and a prism, whose incidence plane and emission plane are connected to the object optical system and the cover glass respectively, that guides image light from the object optical system to the pick-up surface, wherein the electronic endoscope further comprises: a heater that is attached to the prism and heats a surface of the cover glass, to which the emission plane is connected, via the prism; and a controller that controls operations of the heater.

Also, it is favorable that the heater is attached to a reflection plane of the prism.

In addition, it is favorable that the controller actuates the heater for a predetermined period of time at least when a power source of the electronic endoscope is turned on. In this case, it is favorable that the predetermined period of time is the time until the surface of the cover glass to which the emission plane is connected and the surface of the cover glass which is faced to the image pick-up surface enter into thermal equilibrium.

DETAILED DESCRIPTION OF THE INVENTION

Figure 1:
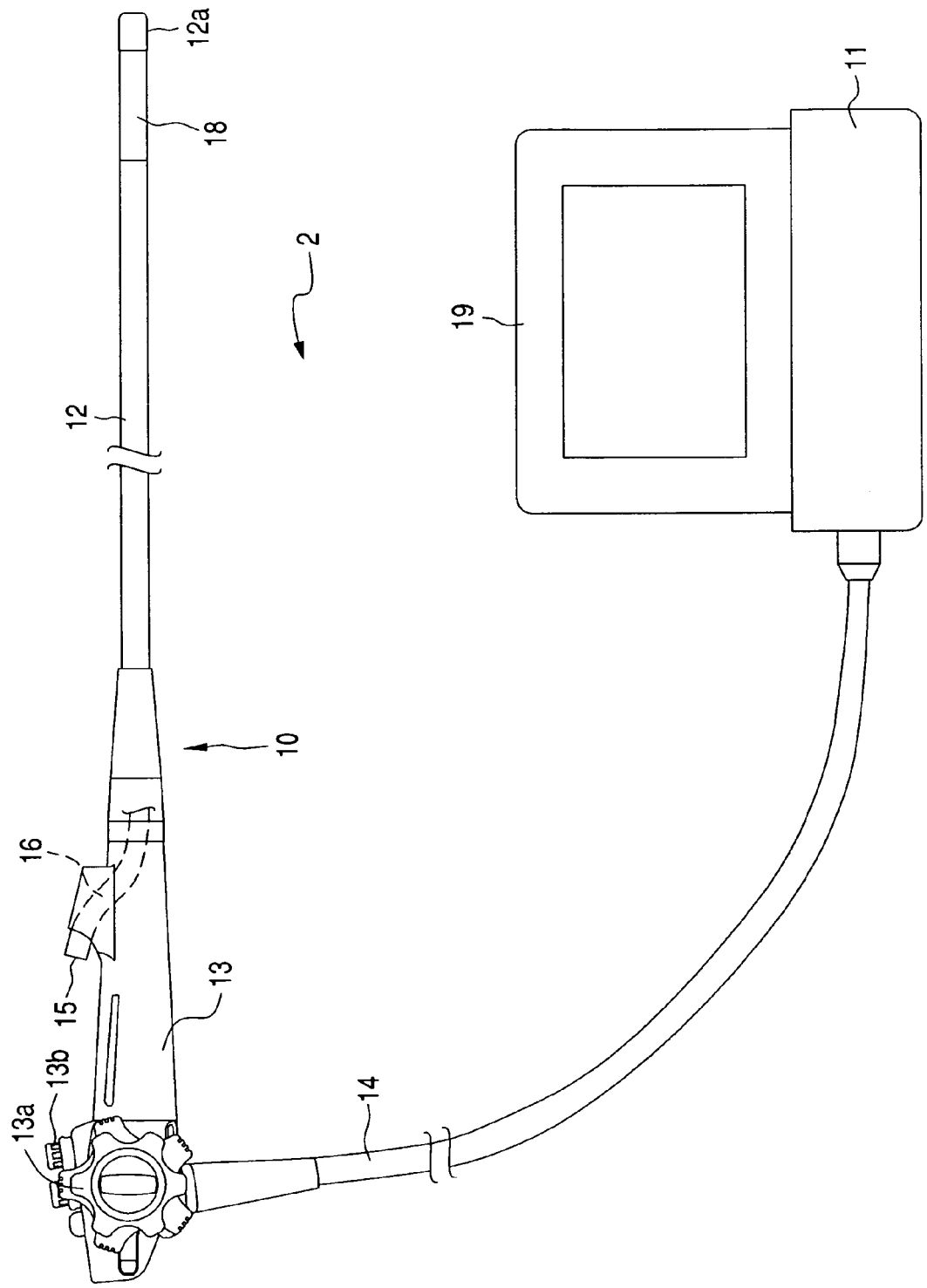
FIG. 1 is a schematic view depicting a configuration of an electronic endoscope system.

In FIG. 1, an electronic endoscope system 2 is composed of an electronic endoscope 10, a processor unit 11, and a light source unit (not shown), etc. The electronic endoscope 10 is provided with an insertion portion 12 inserted into a body cavity, an operation portion 13 linked with and connected to the proximal portion of the insertion portion 12, and cords 14 connected to the processor unit 11 and the light source unit.

A forceps port 15 into which a treatment tool is inserted is provided at the operation portion 13. The forceps port 15 is connected to a forceps channel 16 disposed in the insertion portion 12 as depicted by a dashed line. In addition, an image pick-up unit 17 (Refer to FIG. 2) for picking up an image in a body cavity is internally disposed in the distal end portion 12a linked with the distal end of the insertion portion 12.

A curved portion 18 with which a plurality of curved pieces are linked is provided rearward of the distal end portion 12a. The curved portion 18 makes bending operations in the vertical direction and the horizontal direction by a wire inserted into the insertion portion 12 being pushed and pulled by operating an angle knob 13a secured at the operation portion 13, whereby the distal end portion 12a can be turned to a desired direction in a body cavity.

The processor unit 11 is provided with image processing circuits for applying various types of image processes to image data obtained by digitalizing pick-up signals acquired by the image pick-up unit 17, and the light source unit is provided with a light source for supplying illumination light to the electronic endoscope 10 via cords 14. An image in a body cavity, which is picked up by the image pick-up unit 17, can be observed by a monitor display 19 connected to the processor unit 11.

Figure 2:
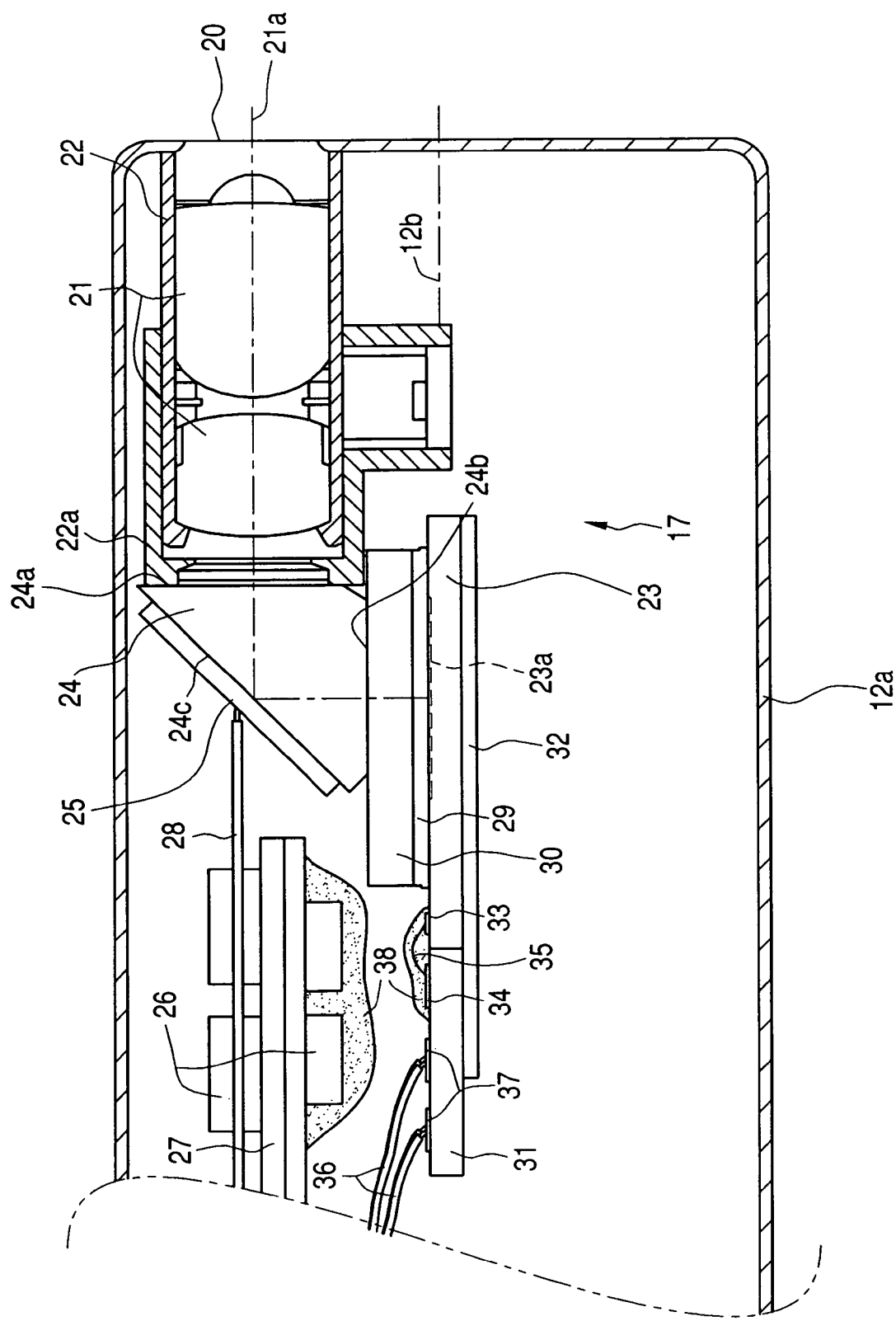
FIG. 2 is a partially enlarged sectional view depicting the construction of the distal end of the insertion portion of an electronic endoscope.

In FIG. 2, an observation window 20 is secured at the distal end portion 12a. A lens barrel 22 for holding an object optical system (lens groups) 21 to take in image light of a portion to be observed in a body cavity is disposed in the observation window 20. The lens barrel 22 is attached so that the optical axis 21a of the object optical system 21 becomes parallel to the center axis 12b of the insertion portion 12. Also, although not shown, the distal end portion 12a is further provided, in addition to the observation window 20, with an illumination window to irradiate illumination light from the light source unit to a portion to be observed in a body cavity, a forceps outlet communicating with the forceps portion 15 via the forceps channel 16, and nozzles for jetting rinse water and air to remove stains of the observation window 20 by operating the air and water-feeding button 13a (Refer to FIG. 1).

A prism 24 for guiding image light of a portion to be observed, which comes through the object optical system 21 via a lens barrel holding frame 22a, to the image pick-up surface 23a of a CCD 23 is connected to the rear end of the lens barrel 22. The prism 24 has its incidence plane 24a connected to the object optical system 21 and its emission plane 24b connected to cover glass 30 described later, respectively. Accordingly, the optical axis 21a of the object optical system 21 and the image pick-up surface 23a are disposed so as to become parallel to each other.

A thin plate type heater 25 is attached to the reflection plane 24c of the prism 24. A transparent plane heating film heater composed of, for example, a chip resistor and ITO, etc., is used for the heater 25. A wire 28 routed from the substrate 27 side on which peripheral circuits 26 such as an AMP 40 and CDS/PGA 42 (Refer to FIG. 4) described later are connected to the heater 25.

The wire 28 is led out from a heat driver 46 (Refer to FIG. 4) described later, which is disposed at a connector portion at the tip end of the cord 14, etc. The heater 25 is supplied with power via the wire 28 and is turned on and off by receipt of a control signal from the heater driver 46.

Figure 3:
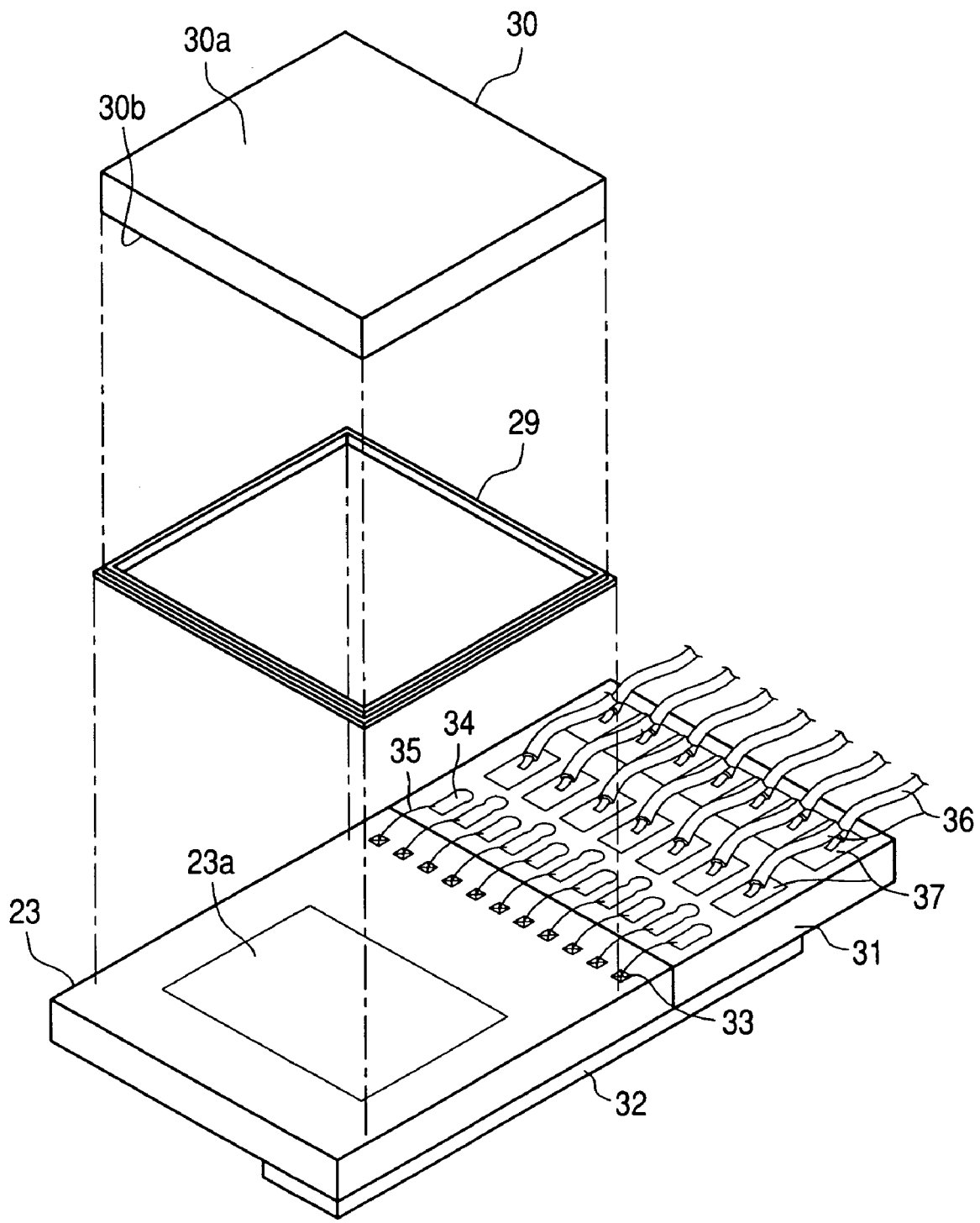
FIG. 3 is a disassembled perspective view depicting the construction of CCD, spacer, cover glass and circuit substrate.

The CCD 23 is composed of, for example, an interline type CCD, and a bare chip having an image pick-up surface 23a secured on its surface is used. As depicted in FIG. 3, rectangular plate type cover glass 30 is attached to the image pick-up surface 23a via a rectangular frame-shaped spacer 29. The CCD 23, spacer 28 and cover glass 30 are adhered to each other with an adhesive agent and assembled together.

A circuit substrate 31 having a thickness roughly equivalent to the thickness of the CCD 23 is adhered to the rear end surface of the CCD 23 by an adhesive agent. A CCD driver 41 (Refer to FIG. 4), etc., described later is mounted in the circuit substrate 31.

A conductive plate 32 is attached to the rear surface of the CCD 23 and the rear surface of the circuit substrate 31 by silver paste. The conductive plate 32 electrically connects the CCD 23 and the circuit substrate 31 to each other via a through-hole (not shown). A drive control signal of an electronic shutter, for example, an overflow drain control signal is inputted from the conductive plate 32 to the CCD 23.

Terminals 33 are concentrated and disposed at the side edge part at the circuit substrate 31 side of the CCD 23. On the other hand, terminals 34 are concentrated and disposed at the side edge part opposite the terminals 33 on the circuit substrate 31. The terminal 33 and terminal 34 are electrically connected to each other by a bonding wire 35. An input/output terminal 37 on which a signal line 36 to input various types of signals into and to output the same from the processor unit 11 via the cord 14 are provided at the rear end side of the terminal 34 of the circuit substrate 31.

The peripheral circuit 26 at the underside of the substrate 27, the terminals 33 and 34 and the bonding wire 35 are sealed by a sealing agent 38. The sealing agent 38 is composed of, for example, one-liquid hardening type epoxy resin.

When producing the image pick-up unit 17, first, the cover glass 30 is attached to the image pick-up surface 23a via the spacer 29. After the cover glass is attached, the circuit substrate 31 is adhered to the rear end surface of the CCD 23. Next, the terminals 33 and 34 are connected to each other by the bonding wire 35, and the terminals 33, 34 and the bonding wire 35 are sealed by the sealing agent 38.

After the sealing agent 38 is coated, the conductive plate 32 is biased to one side and is suspended between the rear side of the CCD 23 and the rear side of the circuit substrate 31. At this time, the CCD 23 and the circuit substrate 31 are electrically connected to each other by the conductive plate 32 via the through-hole secured in the CCD 23 and the circuit substrate 31. Finally, the cover glass 30 is attached by an adhesive agent to the emission plane 24b of the prism 24 connected to the lens barrel holding frame 22a, and a wire 28 is connected to the heater 25.

Figure 4:
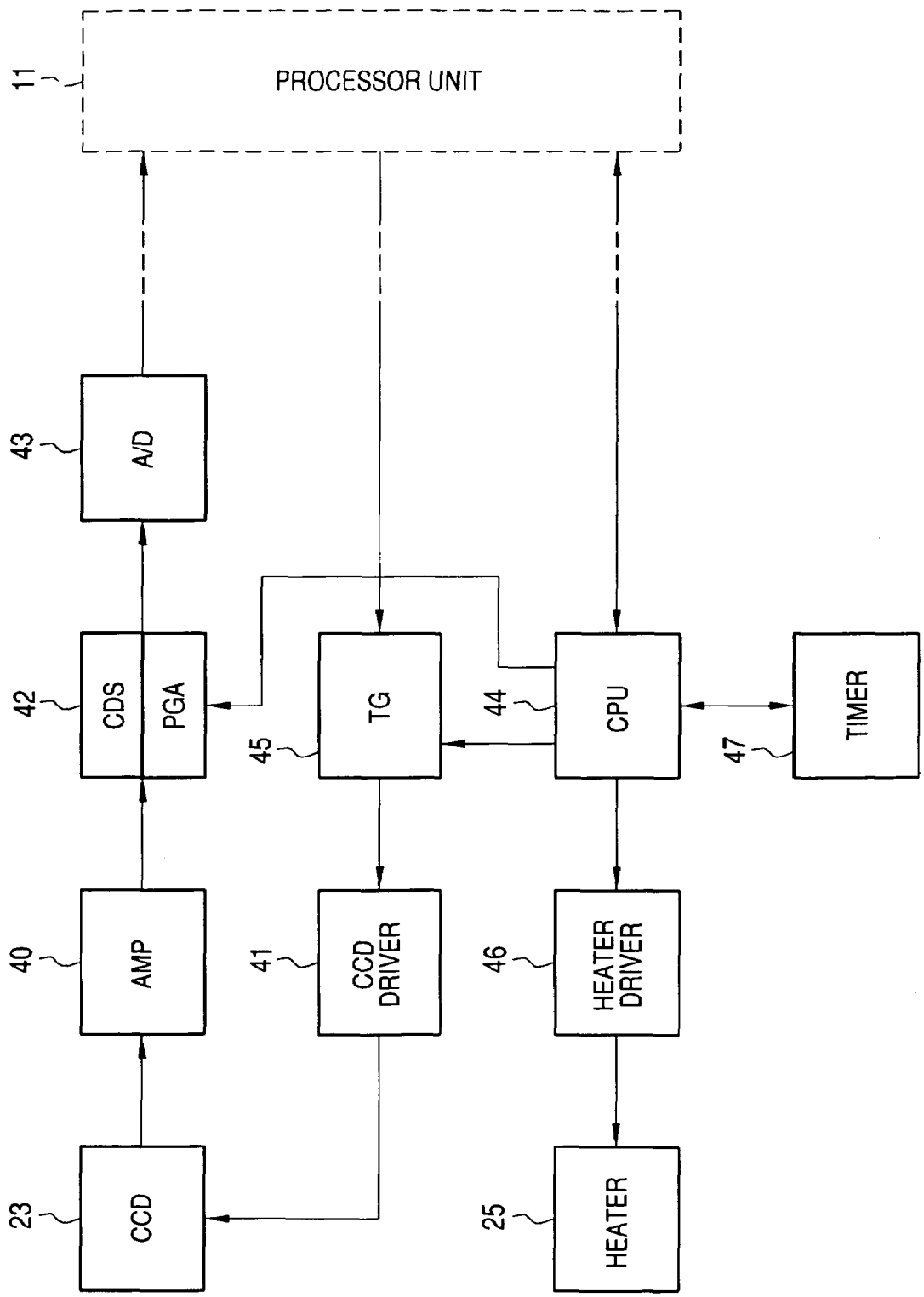
FIG. 4 is a block diagram depicting an electrical configuration of the electronic endoscope.

In FIG. 4, an amplifier (AMP) 40 and a CCD driver 41 are connected to the CCD 23. The amplifier 40 amplifies pick-up signals, which are outputted from the CCD 23, with a predetermined gain, and outputs the same to a correlative double sampling/programmable gain amplifier (CDS/PGA) 42.

The CDS/PGA 42 outputs pick-up signals outputted from the amplifier 40 as image data of R, G and B accurately corresponding to the accumulated electric charge amount of the respective cells of the CCD 23, amplifies the image data and outputs the same to the A/D converter (A/D) 43. The A/D converter 43 converts analog image data outputted from the CDS/PGA 42 to digital image data. The image data digitalized by the A/D converter 43 are transmitted to the processor unit 11 via the cord 14.

A timing generator (TG) 45 controlled by the CPU 44 is connected to the CCD driver 41. The CCD driver 41 controls the shutter speed of an electronic shutter of the CCD 23 by timing signals (clock pulses) inputted from the timing generator (TG) 45.

The CPU 44 receives signals from and transfers the same to the processor unit 11 via the cord 14 and generally controls operations of the respective parts of the electronic endoscope 10. A heater driver 46 and a timer 47 are connected to the CPU 44 in addition to the above-described CDS/PGA 42 and the timing generator (TG) 45.

Upon receipt of control signals from the CPU 44, the heater driver 46 turns on and off the heater 25. The timer 47 operates when the heater 25 is turned on, and transmits a signal, which informs elapse of time, to the CPU 44 after elapse of the time (for example, 30 seconds) until the outer surface 30a (the surface to which the emission plane 24b of the prism 24 is adhered: Refer to FIG. 3) of the cover glass 30 and the inner surface 30b (the surface opposed to the image pick-up surface 23a: Refer to FIG. 3) thereof enter into thermal equilibrium.

When a difference in temperature occurs between the outer surface 30a of the cover glass 30 and the inner surface 30b thereof, and there is a risk that condensation may occur on the inner surface 30b of the cover glass 30, in detail, when the power source of the electronic endoscope 10 is turned on and when rinse water and air is jetted from the nozzle onto the observation window 20 by operating the air and water feeding button 13b, the CPU 44 turns on the heater 25 via the heater driver 46, and turns off the heater 25 upon receipt of a signal transmitted from the timer 47 after a predetermined period of time elapses.

When observing the inside of a body cavity by the electronic endoscope system 2 composed as described above, the insertion portion 12 is inserted into the body cavity. The light source unit is turned on. And an endoscopic image brought about by the CCD 23 is observed on the monitor display 19 while illuminating the inside of the body cavity with the insertion portion 12 inserted thereinto.

The CCD driver 41 is started by turning on the power source of the electronic endoscope 10, and image light of the portion to be observed is picked up by the CCD 23. The image light of the portion to be observed, which is taken in from the object optical system 21, is imaged on the image pick-up surface 23a via the prism 24, whereby a pick-up signal is outputted from the CCD 23.

The pick-up signals outputted from the CCD 23 are amplified by the amplifier 40, are subjected to correlated double sampling and amplification by the CDS/PGA 42, and converted to digital image data by the A/D converter 43.

The image data digitalized by the A/D converter 43 are transmitted to the processor unit 11 via the cord 14, and are subjected to various types of processes by the processor unit 11. After that, the digital data are displayed on the monitor display 19 as an endoscopic image.

When the power source of the electronic endoscope 10 is turned on and when rinse water and air are jetted onto the observation window 20, the heater 25 is turned on by the CPU 44 via the heater driver 46. Simultaneously therewith, the timer 47 starts counting.

And, a signal is transmitted from the timer 47 to the CPU 44 after a predetermined period of time elapses, and the CPU 44 that received the signal transmits a control signal to the heater driver 46 to turn off the heater 25. Thereby, heat of the heater 25 is brought about to the outer surface 30a of the cover glass 30 through the prism 24 to heat the outer surface 30a, wherein the outer surface 30a of the cover glass 30 and the inner surface 30b thereof enter into thermal equilibrium.

As described in detail above, in the electronic endoscope 10, the outer surface 30a of the cover glass 30 is indirectly heated by the heater 25 attached to the prism 24 until the outer surface 30a of the cover glass 30 and the inner surface 30b thereof enter into thermal equilibrium when there is a concern that condensation may occur on the inner surface 30b of the cover glass 30, that is, when the power source of the electronic endoscope 10 is turned on and when rinse water and air are jetted onto the observation window 20. Therefore, it is possible to reliably prevent condensation from occurring on the inner surface 30b of the cover glass 30.

Since the heater 25 is attached to the reflection plane 24c of the prism 24 having a comparatively wide area, utilization efficiency of heat is favorable, wherein it is possible to cope with a radical change in temperature. Further, since the prism 24 is directly attached to the cover glass 30, heat can be uniformly transmitted to the cover glass 30. Additionally, since the rear part of the reflection plane 24c of the prism 24 is made into a dead space where no component is primarily disposed, the space can be effectively utilized.

In addition, a heater may be attached to both sides of the prism 24 and in the vicinity of the CCD 23 at the lower part of the lens barrel 22 instead of or in addition to attaching the heater 25 to the reflection plane 24c of the prism 24. However, in this case, it is necessary to take into consideration positional matching thereof to components disposed at the distal end portion 12 such as the forceps channel 16 and the light guide of illumination light.

In the above-described embodiment, although the heater 25 is turned on when the power source is turned on and when rinse water and air are jetted onto the observation window 20, the heater 25 may be manually turned on and off by an operator of the electronic endoscope 10.

Although, in the above-described embodiment, a spacer 29 is provided to secure an air gap between the CCD 23 and the cover glass 30, a transparent adhesive agent may be used instead of the spacer 29, or legs maybe formed on the cover glass 30. In addition, although the circuits such as the amplifier 40 and the CCD driver 41 are mounted at the electronic endoscope 10 side, the circuits may be provided at the processor unit 11 side.

Also, in the above-described embodiment, a description was given of an example of using a so-called direct-viewing type electronic endoscope 10 in which the optical axis 21a of the object optical system 21 is attached so as to become parallel to the center axis 12b of the insertion portion 12. However, the present invention may be applicable to a side-viewing type electronic endoscope in which the center axis 12b is made vertical to the optical axis 21a.

According to an electronic endoscope of the present invention, since the electronic endoscope includes a heater, attached to the prism whose incidence plane and emission plane are connected to the object optical system and the cover glass, respectively, for heating the surface of the cover glass to which the emission plane is connected via the prism, and a controller for controlling operations of the heater, the electronic endoscope has an inexpensive structure and is capable of efficiently and reliably preventing condensation of the cover glass attached to a solid-state image pick-up device.

The entire disclosure of each and every foreign patent application from which the benefit of foreign priority has been claimed in the present application is incorporated herein by reference, as if fully set forth.

What is claimed is:

1. An electronic endoscope comprising a pick-up unit at a distal end of the electronic endoscope, the pick-up unit comprising:

an object optical system that brings in image light of a portion to be observed in a body cavity;

a solid-state image pick-up device that picks up the image light and outputs image pick-up signals;

a cover glass disposed above an image pick-up surface of the solid-state image pick-up device with spacing secured between the cover glass and the image pick-up surface; and a prism, whose incidence plane and emission plane are connected to the object optical system and the cover glass respectively, that guides image light from the object optical system to the pick-up surface, wherein the electronic endoscope further comprises:

a heater that is attached to the prism and heats a surface of the cover glass, to which the emission plane is connected, via the prism; and a controller that controls operations of the heater.

2. The electronic endoscope according to claim 1, wherein the heater is attached to a reflection plane of the prism.

3. The electronic endoscope according to claim 1, wherein the controller actuates the heater for a predetermined period of time at least when a power source of the electronic endoscope is turned on.

4. The electronic endoscope according to claim 3, wherein the predetermined period of time is the time until the surface of the cover glass to which the emission plane is connected and the surface of the cover glass which is faced to the image pick-up surface enter into thermal equilibrium.

* * * * *